United States Patent [19]

Schwartz et al.

[11] 4,444,793
[45] * Apr. 24, 1984

[54] FERMENTATION OF WHEY TO PRODUCE A THICKENING AGENT

[75] Inventors: Robert D. Schwartz, Concord; Elizabeth A. Bodie, El Cerrito, both of Calif.

[73] Assignee: Stauffer Chemical Company, Westport, Conn.

[*] Notice: The portion of the term of this patent subsequent to Aug. 16, 2000 has been disclaimed.

[21] Appl. No.: 290,766

[22] Filed: Aug. 7, 1981

[51] Int. Cl.³ .................... A23C 21/02; C12P 19/04; C12P 19/08; C12N 1/20
[52] U.S. Cl. ........................................ 426/41; 426/43; 435/101; 435/103; 435/253
[58] Field of Search .............. 435/101, 103, 245, 253; 426/41, 43

[56] References Cited

U.S. PATENT DOCUMENTS 2,789,911  4/1957  Toulmin, Jr. ................ 435/103 X
3,044,940  7/1962  Behrens et al. ................ 435/103

OTHER PUBLICATIONS

Stauffer, et al., Extracellular Microbial Polysaccharide Production by Fermentation on Whey or Hydrolyzed Whey, J. Food Sci., vol. 43, 1978, (pp. 756–758).
Lundstedt, E., Citrated Whey Starters, J. Dz. Sci., vol. 45, 1962 (pp. 1320–1326).
Manual for Dairy Manufacturing Short Courses, Litho. in U.S.A., Kurtz Bros., Clearfield, Pa., 1956 (pp. 56–57).
Lawford, et al., Dextron Biosynthesis and Dextronsucrage Production by Continuous Culture of *Leuconostoc mesenteroides*, Biotechnol. and Bioeng., vol. XXI, 1979 (pp. 1121–1131).

*Primary Examiner*—David M. Naff
*Attorney, Agent, or Firm*—Michael J. Bradley

[57] ABSTRACT

Dairy whey, a waste product of cheese production, is fermented to produce a thickening agent for use in the food industry by forming a fermentation broth containing whey and sucrose, and fermenting the broth with *Leuconostoc mesenteroides* ATCC 14935. The fermentation broth can optionally contain a water-soluble phosphate as a pH buffer and yeast extract.

9 Claims, 3 Drawing Figures

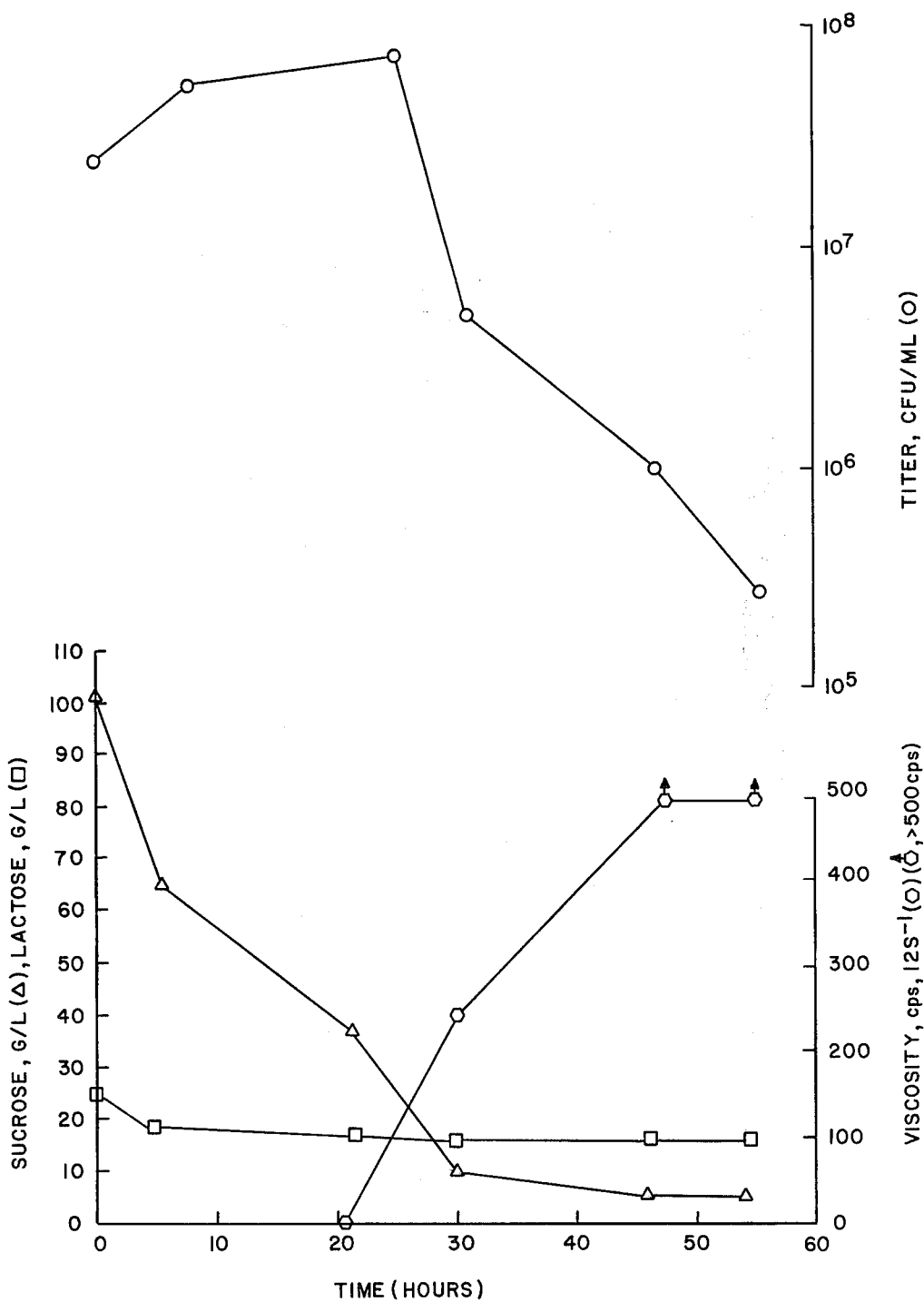
FIGURE I
L. MESENTEROIDES ATCC-14935 FERMENTATION
IN WHEY-SUCROSE MEDIUM WITHOUT $K_2HPO_4$

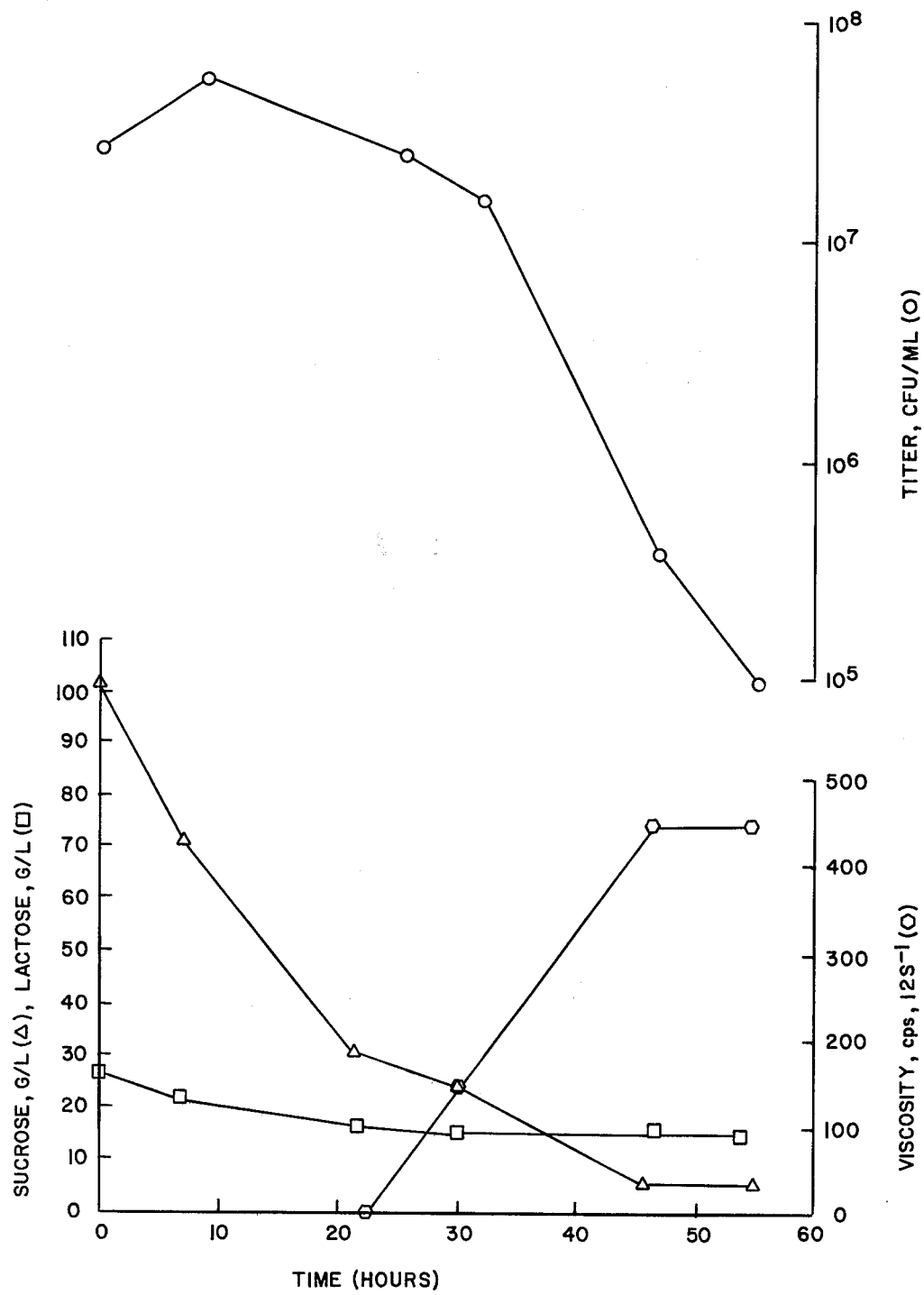
FIGURE II
L. MESENTEROIDES ATCC-14935 FERMENTATION IN WHEY-SUCROSE MEDIUM WITHOUT $K_2HPO_4$ FIGURE III
VISCOSITY VS. SHEAR RATE CURVE FOR DRIED FUNCTIONALIZED WHEY
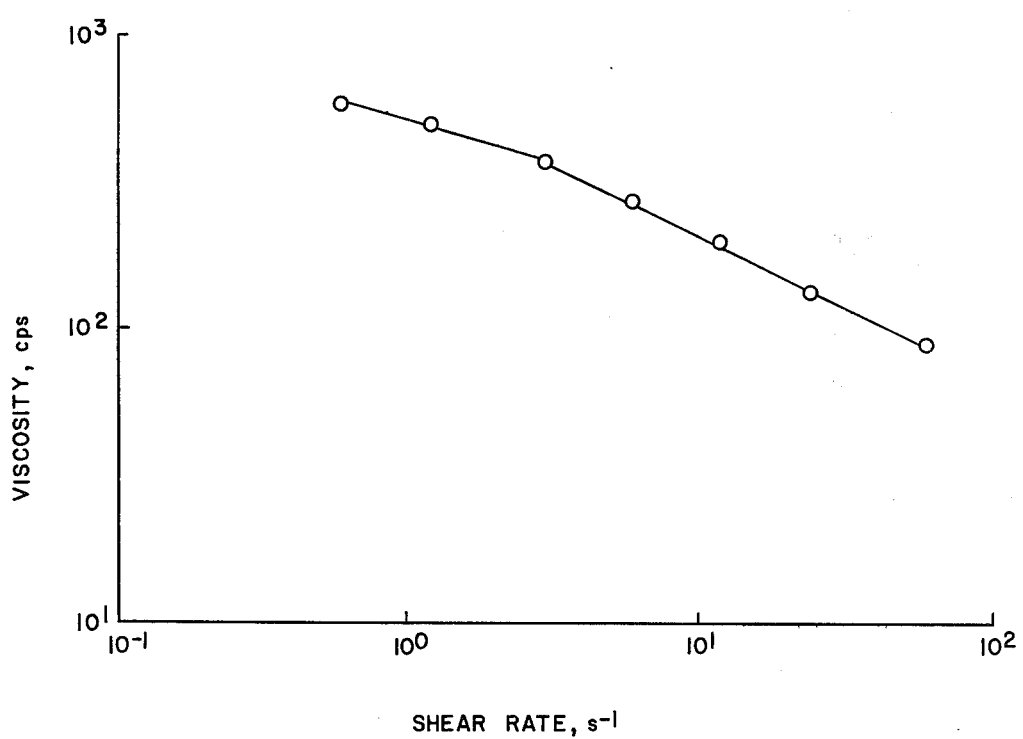

FERMENTATION OF WHEY TO PRODUCE A THICKENING AGENT

BRIEF DESCRIPTION OF THE INVENTION

The process of this invention provides a method of functionalizing whey by forming a fermentation broth of the whey, sucrose and optionally water-soluble phosphate as a pH buffer, and yeast extract and then fermenting this whey broth with the organism *Leuconostoc mesenteroides* strain ATCC 14935 on deposit with the American Type Culture Collection, Rockville, Md.

BACKGROUND OF THE INVENTION

Controlled fermentation of food can be used as a means of improving functionality of food. Dairy whey, a food, may be an economical source of a fermentable substrate, and is widely used as an accepted milk-derived ingredient in manufactured foods. If whey can be functionalized by fermentation with an organism that produces a thickening polymer when grown on the whey substrate, it is possible to obtain whey products that may serve the function of a stabilizer, thickener, emulsifier, or flavor enhancer.

Whey is the fluid medium containing a very low concentration of milk solids and a high concentration of lactose. Disposal of this waste by-product by drying is an energy-intensive, expensive procedure which results in an expensive by-product. Sewering of the whey is prohibitive in cost due to the high biological oxygen demand which is placed on municipal sewer systems.

The most desirable method of handling a whey waste stream is to produce a high quality natural food ingredient from the whey waste product. Applicant has discovered a novel method of producing a functionalized whey product for use as a food ingredient or any type of product where milk solids and lactose are acceptable ingredients.

DESCRIPTION OF THE DRAWINGS

FIG. I shows a graph of a fermentation of *Leuconostoc mesenteroides* ATCC 14935 in a medium containing 4% Teklac (whey), 10% sucrose, 0.1% $K_2HPO_4$, and 0.05% yeast extract.

FIG. II shows a graph of a fermentation of *L. mesenteroides* ATCC 14935 in a medium containing 4% Teklac (whey), 10% sucrose, and 0.05% yeast extract.

FIG. III shows a viscosity vs. shear rate curve for a typical dried functionalized whey produced by the fermentation techniques of this invention.

DETAILED DESCRIPTION OF THE INVENTION

A functionalized dairy whey product having a viscosity greater than 200 centipoise at a $12s^{-1}$ shear rate for use as a food ingredient that may serve as a stabilizer, thickener, or emulsifier, can be produced by fermenting a mixture comprising whey, sucrose, optionally yeast extract and a pH buffer with the organism *Leuconostoc mesenteroides* ATCC 14935 to produce a functionalized whey product containing a thickening polymer produced by the organism *Leuconostoc mesenteroides* ATCC 14935.

Dextrans are polyglucans that are synthesized from sucrose by many species of the genera Leuconostoc, Lactobacillus, and Streptococcus. The synthesis occurs extracellularly and is catalyzed by a species specific enzyme, dextransucrase. Soluble and insoluble dextrans are produced and molecular weights range from $1.5 \times 10^4 - 2 \times 10^7$ and higher. Although dextran has the potential to be used in food products as a conditioner, stabilizer, "bodying agent," etc., it has not found wide commercial use in the food industry. Dextran has been used in gel filtration processes to concentrate proteins or to recover proteins from liquid wastes, including cheese whey fractionation. Dextran solutions are reported to have properties similar to locust bean gum; see, Brooker, 1979, "Electron Miscroscopy of Dextrans Produced by Lactic Acid Bacteria," *Microbial Polysaccharides and Polysaccharases*, Berkeley et al. Eds, pp. 84–115, Academic Press, N.Y.; Jeans, 1977, "Dextrans and Pullulans: Industrially Significant D-glucans," *Extracellular Microbial Polysaccharides*, Sanford et al. Eds., pp. 284–298, ACS, Washington, D.C.; Kang et al., 1979, "Polysaccharides," *Microbial Technology*, 2nd Ed., Vol. 1. pp. 417–481, Academic Press, N.Y.; Lawford et al., 1979, "Dextran Biosynthesis and Dextransucrase Production by Continuous Culture of *Leuconostoc mesenteroides*," *Biotech. Bioeng.* 21:1121–1131; and Wells, 1977, "Extracellular Microbial Polysaccharides—A Critical Overview," *Extracellular Microbial Polysaccharides*, ACS Symposium Series 45, pp. 299–313, ACS, Washington, D.C.

Fermentation of a whey broth comprising unhdyrolyzed whey (acid or sweet), sucrose, and optionally yeast extract and phosphate results in polymer formation and functionalization of the whey so that the whey product can be utilized as a food ingredient. This anaerobic fermentation can be carried out preferably in a pH range of 5.5 to 7.5, preferably with the pH maintained in a range from about 6.0 to about 7.0. The fermentation can be carried out at a temperature from about 20° to 35° C., preferably carried out at a temperature from about 25° to about 30° C. Typical composition of Teklac (sweet dairy whey) is as follows:

| CHEMICAL AND PHYSICAL SPECIFICATIONS | |
|---|---|
| Ingredient Listing: Whey | |
| *Typical Proximate Analysis* | |
| Protein (N × 6.38)% | 12.7 |
| Fat % | 1.1 (1.25% Maximum) |
| Moisture % | 4.5 (5.0% Maximum) |
| Ash % | 8.0 |
| Lactose % | 71.3 |
| Calories, Cal/100 g | 350.0 |
| *Typical Vitamin & Mineral Analysis* | |
| Vitamin A I.U./100 g | Nil |
| Vitamin C mg/100 g | Nil |
| Thiamin mg/100 g | 0.40 |
| Riboflavin mg/100 g | 1.76 |
| Niacin mg/100 g | 1.00 |
| Calcium % | 0.71 |
| Iron % | Nil |
| Vitamin $B_{12}$ ug/100 g | 2.12 |
| Phosphorus % | 0.69 |
| Pantothenic Acid mg/100 g | 4.09 |
| *Microbiological Standards* | |
| Standard Plate Count | 10,000/g (Maximum) |
| Coliforms | 9/g (Maximum) |
| *E. coli* | Negative |
| Salmonella | Negative |

The nutritional values listed above are within 80% of the value declared in compliance with Federal Nutritional Regulations 21 CFR §1.17(4)(ii).

|                              | Typical Range | Limit         |
|------------------------------|---------------|---------------|
| Solubility Index             | 0.1–0.5 ml    | 1.25 ml Max.  |
| Acidity                      | 0.10–0.14%    | 0.16 Max.     |
| Alkalinity of Ash            | 175–200 ml    | 225 ml Max.   |
| Scorched Particles           | 7.5 mg        | 15.0 mg Max.  |
| Particle size (Through 40 Mesh) | 99–100%    | 98% Min.      |

Concentration of whey can range from about 0.5% to about 12.0%, preferably from about 1% to about 3%, and the concentration of added sucrose can range from about 5.0% to about 20.0%, preferably 8% to 12%. The concentration of the optional yeast extract in the fermentation broth can range from about 0 to about 0.5%, preferably from about 0.01% to about 0.05%. Concentration of optional phosphate can range from 0 to about 0.25% $K_2HPO_4$ as desired. Adequate fermentation broth viscosities (>200 cps and preferably >800 cps at a 12 $s^{-1}$ shear rate) are usually reached within 30 to 50 hours. All of the above weight percents are in weight per volume.

EXAMPLE 1

FIG I shows a typical fermentation of a whey-sucrose broth medium containing 4% Teklac, 10% sucrose, 0.1% $K_2HPO_4$ and 0.05% yeast extract that has been fermented with *Leuconostoc mesenteroides* ATCC 14935. The medium was sterilized by autoclaving at 15 pounds per square inch (psi) for 20 minutes. The sucrose was sterilized and added separately. The pH was adjusted to 7.0 before autoclaving. $NH_4OH$ (6%) was used to prevent the pH from falling below 6.0. The fermentation was anaerobic (no gas sparged), with agitation speed 120 rpm. The temperature was maintained between 25°–27° C. The inoculum was a 20-hour-old culture grown in 10% sucrose, 0.5% $K_2HPO_4$, 0.25% yeast extract, and 0.01% $MgSO_4$. A Bio-flow ® fermentor was used (New Brunswick Scientific Co., N.J.). The figure shows that within 46 hours, a viscosity greater than 500 cps (at a 12$s^{-1}$ shear rate) was observed. More than 95% of the sucrose was utilized and 40% of the lactose was consumed.

EXAMPLE 2

FIG. II shows a typical fermentation of a whey-sucrose medium containing 4% Teklac, 10% sucrose, and 0.05% yeast extract. The medium was sterlized by autoclaving at 15 psi for 20 minutes. The sucrose was sterilized and added separately. The pH was adjusted to 7.0 before autoclaving. $NH_4OH$ (6%) was used to prevent the pH from falling below 6.0. The fermentation was anaerobic (no gas sparged), with agitation speed 120 rpm. The temperature was maintained between 25°–27° C. The inoculum was a 20-hour-old culture grown in 10% sucrose, 0.5% $K_2HPO_4$, 0.25% yeast extract, and 0.01% $MgSO_4$. A Bio-flow ® fermentor was used as in Example 1. The figure shows that within 46 ours, a viscosity of 460 cps was obtained. About 95% of the sucrose was utilized and 44% of the lactose was consumed.

The high viscosity broths produced by fermentation techniques of this invention may be dried and/or sterilized by autoclaving plus lyophilization, spray drying, or other techniques.

EXAMPLE 3

A viscosity versus shear rate curve for a typical dried functionalized whey so produced is shown in FIG. III. The sample was tested on a 2.5 XLVT Wells-Brookfield microviscometer having a 3° cone at 25° C. The sample size was 2.0 milliliters. The sample consisted of a 10.0% solution (weight/vol) of functionalized whey in deionized water. The pH was 6.9. The increase in viscosity with decrease in shear rate is typical of pseudoplastic polymers.

The functionalized whey product of this invention can be used as a food ingredient where milk solids and/or whey, and/or thickeners, and/or stabilizers are used such as in ice cream, salad dressing, foam stabilizers (meringue), puddings, snack foods, etc.

What is claimed is:
1. A process for producing a functionalized dairy whey product comprising the steps of:
   (a) forming a fermentation broth of whey, and sucrose; and
   (b) fermenting the broth with the organism *Leuconostoc mesenteroides* ATCC 14935 to produce a functionalized dairy whey product containing a thickening polymer produced by the organism.
2. The process of claim 1 wherein the concentration of the whey is from about 0.5% to about 12% weight per volume and the sucrose is from about 5% to about 20% weight per volume.
3. The process of claim 1 wherein an additional ingredient of the fermentation broth is yeast extract.
4. The process of claim 1 wherein an additional ingredient of the fermentation broth is up to about 0.5% weight per volume of yeast extract.
5. The process of claim 1 wherein an additional ingredient of the fermentation broth is $K_2HPO_4$.
6. The process of claim 1 wherein an additional ingredient of the fermentation broth is up to about 0.25% weight per volume $K_2HPO_4$.
7. The process of claim 1 wherein the fermentation is conducted at a temperature of from about 20° to about 35° C.
8. The process of claim 1 wherein the fermentation is conducted at a temperature of from about 20° to about 35° C. and the pH is maintained in a range of from about 5.5 to about 7.5.
9. The process of claim 1 plus the additional step:
   (c) drying said functionalized whey product to form a dry functionalized whey product.

* * * * *